United States Patent [19]

Takasugi et al.

[11] Patent Number: 5,145,860
[45] Date of Patent: Sep. 8, 1992

[54] THIAZOLE COMPOUNDS AND PHARMACEUTICAL COMPOSITION COMPRISING THE SAME

[75] Inventors: Hisashi Takasugi; Shigetaka Nishino, both of Osaka; Akito Tanaka, Takarazuka, all of Japan

[73] Assignee: Fujisawa Pharmaceutical Co., Ltd., Osaka, Japan

[21] Appl. No.: 495,622

[22] Filed: Mar. 19, 1990

Related U.S. Application Data

[63] Continuation-in-part of Ser. No. 451,935, Dec. 18, 1989, abandoned.

[30] Foreign Application Priority Data

Jan. 5, 1989 [GB] United Kingdom ............... 8900191
Mar. 22, 1989 [GB] United Kingdom ............... 8906575
Dec. 4, 1989 [GB] United Kingdom ............... 8927351

[51] Int. Cl.$^5$ ............... A61K 31/425; C07D 277/24
[52] U.S. Cl. ............... 514/365; 548/200; 548/204
[58] Field of Search ............... 514/365; 548/200, 204

[56] References Cited

U.S. PATENT DOCUMENTS 4,098,898 7/1978 Durant ............... 548/336 X
4,166,856 9/1979 Durant ............... 548/204 X
4,168,315 9/1979 Rynbrandt ............... 544/369 X

FOREIGN PATENT DOCUMENTS 1-75475 3/1989 Japan .
1188846 4/1970 United Kingdom .

OTHER PUBLICATIONS

Justus Liebigs Annalen Der Chemie, vol. 679, 1964, pp. 144–150, Weinheim, Del T. Pyl et al.: "Über bicyclische Heterocyclen mit gemeinsamem Stickstoffatom, IX$^1$ Zur Kenntnis der Imidazo [5.1–b] thiazole" pp. 145,148, compound IIb.

*Primary Examiner*—Mary C. Lee
*Assistant Examiner*—Jacqueline Haley
*Attorney, Agent, or Firm*—Oblon, Spivak, McClelland, Maier & Neustadt

[57] ABSTRACT

The invention relates to new thiazole compounds, of antithrombotic, vasodilating, antiallergic, antiinflammatory and 5-lipoxygenase inhibitory activity, of the formula:

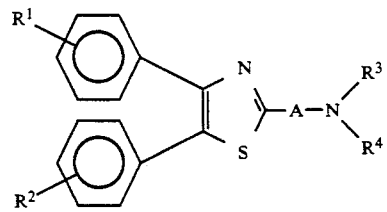

wherein A is lower alkylene or carbonyl;
$R^1$ and $R^2$ are each halogen, lower alkyloxy, lower alkylthio or lower alkylsulfinyl;
$R^3$ is acyl derived from an aliphatic carboxylic or carbamic acid; and
$R^4$ is hydrogen, lower alkyl, amidino or acyl derived from an aliphatic carboxylic or carbamic acid, or the pharmaceutically acceptable salt thereof.

5 Claims, No Drawings

THIAZOLE COMPOUNDS AND PHARMACEUTICAL COMPOSITION COMPRISING THE SAME

This application is a continuation-in-part of Ser. No. 07/451,935 filed Dec. 18, 1989, now abandoned.

This invention relates to new thiazole compounds. More particularly, this invention relates to new thiazole compounds and pharmaceutically acceptable salts thereof which have pharmacological activities, processes for preparation thereof, a pharmaceutical composition comprising the same and a use of the same.

Accordingly, one object of this invention is to provide the new and useful thiazole compounds and pharmaceutically acceptable salts thereof which possess antithrombotic, vasodilating, antiallergic, anti-inflammatory and 5-lipoxygenase inhibitory activities.

Another object of this invention is to provide processes for preparation of the thiazole compounds and salt thereof.

A further object of this invention is to provide a pharmaceutical composition comprising said thiazole compounds or a pharmaceutically acceptable salt thereof.

Still further object of this invention is to provide a use of said thiazole compound or a pharmaceutically acceptable salts thereof as a medicament for prophylactic and therapeutic treatment of thrombosis, hypertension, cardiovascular or cerebrovascular diseases, allergy and inflammation, particularly thrombosis, in human being and animals.

The object thiazole compounds of the present invention are novel and represented by the following general formula:

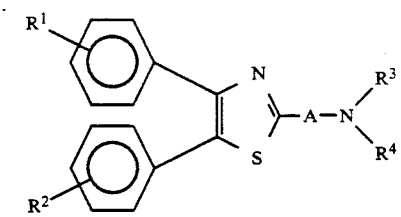

wherein
- A is lower alkylene or carbonyl,
- $R^1$ and $R^2$ are each halogen, lower alkyloxy, lower alkylthio, or lower alkylsulfinyl,
- $R^3$ is amino-protective group, and
- $R^4$ is hydrogen, lower alkyl which may have heterocyclic group, piperidyl which may have suitable substituent(s), amidino or amino-protective group.

The object compound (I) of the present invention can be prepared by the following processes.

Process (a)

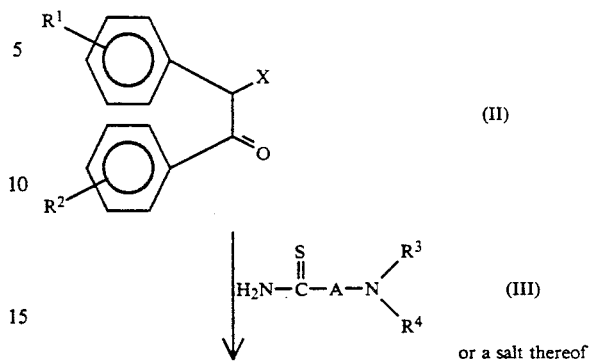

Process (b)

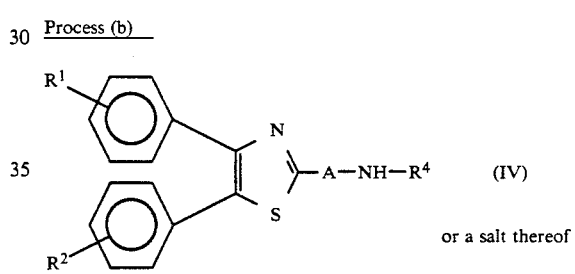

Process (c)

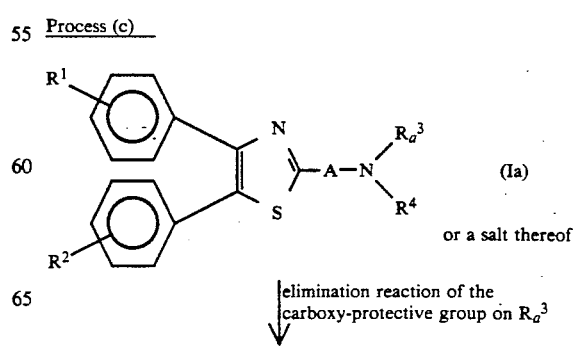

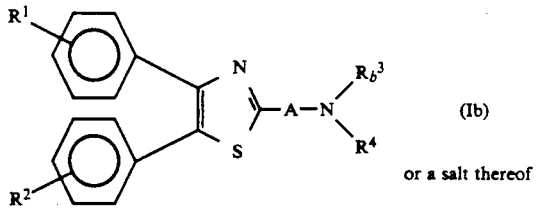

or a salt thereof wherein

A, $R^1$, $R^2$, $R^3$ and $R^4$ are each as defined above,
$R_a^3$ is protected carboxy(lower)alkanoyl,
$R_b^3$ is carboxy(lower)alkanoyl, and
X is an acid residue.

In the present invention, with regard to the object compound (I), (Ia) and (Ib), and the starting compound (IV) and when A is lower alkylene, it is to be understood that there may be tautomeric equilibrium between the partial structures of such compound as follows.

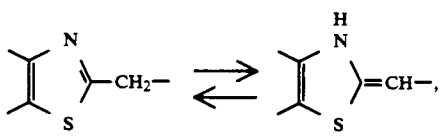

and such tautomer is also included within the scope of the present invention.

However, in the present invention, the partial structure of the compounds (I), (Ia), (Ib), and (IV) in case A is lower alkylene, are represented by the following one expression for convenient sake,

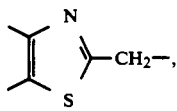

and the compounds (I), (Ia), (Ib) and (IV) are named on the basis of such formula, when A is lower alkylene.

Suitable salts of the compounds (I), (Ia), (Ib), or (IV) are conventional non-toxic, pharmaceutically acceptable salts and may include e.g. a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt, (e.g. triethylamine salt, pyridine salt, picoline salt, ethanolamine salt, triethanolamine salt, dicyclohexylamine salt, N,N'-dibenzylethylenediamine salt, etc.); an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and lower alkyl moiety in the term "lower alkyloxy", "lower alkylthio", "lower alkylsulfinyl" and "lower alkyl which may have heterocyclic group" may include straight or branched one having 1 to 6 carbon atom(s), such as methyl, ethyl, propyl, iso-propyl, butyl, iso-butyl, sec-butyl, tert-butyl, pentyl, tert-pentyl, hexyl, and the like, preferably one having 1 to 4 carbon atom(s), and the most preferably methyl.

Suitable "lower alkylene" may be straight or branched one having 1 to 6 carbon atom(s), such as methylene, ethylene, trimethylene, propylene, tetramethylene, pentamethylene, hexamethylene, dimethylmethylene and the like, preferably one having 1 to 4 carbon atom(s), and the most preferably methylene, ethylene and dimethylmethylene.

Suitable "halogen" may be fluorine, chlorine, bromine or iodine.

Suitable "amino-protective group" may include acyl such as aliphatic acyl, aromatic acyl, heterocyclic acyl, aliphatic acyl substituted with aromatic or heterocyclic group, which are derived from carboxylic, sulfonic and carbamic acid, and the like.

The aliphatic acyl may include: lower alkanoyl which may have one or more suitable substituent(s) such as carboxy, protected carboxy, and the like, preferably lower alkanoyl (e.g. formyl, acetyl, propionyl, butyryl, iso-butyryl, valeryl, iso-valeryl pivaloyl, hexanoyl, etc.), carboxy(lower)alkanoyl (e.g. carboxyacetyl, carboxypropionyl, carboxybutyryl, carboxyhexanoyl, etc.) protected carboxy(lower)alkanoyl, in which the carboxy-protective group is a conventional one used in this field, for example, esterified carboxy(lower)alkanoyl such as lower alkoxycarbonyl(lower)alkanoyl (e.g. methoxycarbonylacetyl, ethoxycarbonylacetyl, ethoxycarbonylpropionyl, etc.); lower alkylthio(lower)alkanoyl (e.g. (methylthio)acetyl, (ethylthio)acetyl, (propylthio)acetyl, (methylthio)propionyl, (ethylthio)propionyl, etc.); carbamoyl which may have lower alkyl (e.g. carbamoyl, methylcarbamoyl, ethylcarbamoyl, propylcarbamoyl, iso-propylcarbamoyl, butylcarbamoyl, iso-butylcarbamoyl, sec-butylcarbamoyl, pentylcarbamoyl, tert-pentylcarbamoyl, hexylcarbamoyl, etc.); lower alkoxycarbonyl having 2 to 7 carbon atoms (e.g. methoxycarbonyl, ethoxycarbonyl, propoxycarbonyl, 1-cyclopropylethoxycarbonyl, iso-propoxycarbonyl, butoxycarbonyl, t-butoxycarbonyl, pentyloxycarbonyl, t-pentyloxycarbonyl, hexyloxycarbonyl, etc.), preferably one having 3 to 6 carbon atoms; lower alkanesulfonyl (e.g., mesyl, ethanesulfonyl, propanesulfonyl, iso-propanesulfonyl, butanesulfonyl, etc.); cyclo(lower)alkyl(lower)alkanoyl (e.g. cyclohexylacetyl, cyclopentylacetyl, etc.); lower alkenoyl (e.g. acryloyl, crotonoyl, etc.); and the like.

The aromatic acyl may include aroyl which may have one or more suitable substituent(s) such as nitro (e.g. benzoyl, toluoyl, xyloyl, naphthoyl, nitrobenzoyl, dinitrobenzoyl, nitronaphthoyl, etc.), arenesulfonyl which may have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and the like.

The heterocyclic group in "heterocyclic acyl" may include aliphatic or aromatic, heteromonocyclic or heteropolycyclic group containing at least one hetero atom such as nitrogen, oxygen and sulfur atoms, which may have suitable substituent(s), and more suitable heterocyclic group thus defined may include 5 to 7 membered aliphatic heteromonocyclic group having one to three atom(s) selected from nitrogen, oxygen and sulfur or 5 to 10 membered aromatic heteromono- or bi-cyclic group having one to three hetero atom(s) selected from nitrogen, oxygen and sulfur, such as morpholino; morpholinyl; thiazolidinyl which may have oxo group(s) (e.g. thiazolidin-2-yl, thiazolidin-3-yl, thiazolidin-4-yl, thiazolidin-5-yl, 1,1,4-trioxothiazolidin-3-yl, etc.); piperidino; piperidyl; piperazinyl; pyridyl; thiazolyl which may have amino group (e.g. thiazol-2-yl, thiazol-4-yl, thiazol-5-yl, 2-aminothiazol-4-yl, etc.); pyridazinyl; dihydro- or tetrahydropyridazinl which may have oxo and/or lower alkyl group(s) (e.g. 1,4,5,6-tetrahydropyridazin-3-yl, 1,4,5,6-tetrahydro-6-oxopyridazin-3-yl, 2,3-dihydro-6-methyl-3-oxopyridazin-4-yl, etc.); imidazopyridyl which may have lower alkyl group (e.g. imidazo[1,2-a]pyridin-2-yl, 7-mathylimidazo[1,2-a]pyridin-2-yl, imidazo[4,5-c]pyridin-2-yl, etc.); and the like.

The aliphatic acyl substituted with aromatic group may include ar(lower)alkanoyl (e.g. phenylacetyl, phenylpropionyl, naphtylacetyl, etc.);

arylthio(lower)alkanoyl (e.g. (phenylthio)acetyl, (phenylthio)propionyl, etc.);

arylsulfonylamino(lower)alkanoyl [e.g. N-(benzenesulfonyl)glycyl, N-(p-toluenesulfonyl)glycyl, etc.]; and the like.

The aliphatic acyl substituted with heterocyclic group may include aliphatic acyl such as the ones defined above, which is substituted with the heterocyclic group such as the ones defined in "heterocyclic group" described before, and preferably the ones such as pyridyl(lower)alkanoyl (e.g. (3-pyridyl)acetyl, etc.); pyridyl(lower)alkenoyl (e.g. 3-[3-pyridyl]acryloyl, etc.); amino-substituted thiazolyl(lower)alkanoyl (e.g. (2-aminothiazol-4-yl)acetyl, etc.); thiazolidinyl(lower alkanoyl which may have oxo groups (e.g. (thiazolidin-3-yl)acetyl, (1,1,4-trioxothiazolidin-3-yl)acetyl, etc.); imidazopyridyl(lower)alkanoyl (e.g. which may have lower alkyl (7-methylimidazo[1,2-a]pyridin-2-yl)acetyl, etc.); and the like.

The "acid residue" may include halogen (e.g. chlorine, bromine, iodine or fluorine); acyloxy such as lower alkanoyloxy (e.g. acetoxy, etc.), lower alkanesulfonyloxy (e.g. methanesulfonyloxy, etc.), and the like, and preferably halogen.

The "protected carboxy(lower)alkanoyl" and "carboxy(lower)alkanoyl" may include the same, which are described in the above.

The heterocyclic group in "lower alkyl which may have heterocyclic group" may include the same, which are exemplified in "heterocyclic acyl" stated above.

Suitable substituent on "piperidyl" may include amino; hydroxy; nitro; cyano; lower alkyl as exemplified above; lower alkoxy as exemplified above; hydroxy(lower)alkyl in which the lower alkyl moiety may be the same as those exemplified above; acyl(lower)alkyl, the acyl group of which may be the same as those exemplified below, preferably carbamoyl(lower)alkyl (e.g. carbamoylmethyl, carbamoylethyl, etc.), lower alkylcarbamoyl(lower)alkyl (e.g. methylcarbamoylmethyl, ethylcarbamoylmethyl, propylcarbamoylmethyl, iso-propylcarbamoylmethyl, methylcarbamoylethyl, etc.); oxo; acyl as exemplified below, preferably lower alkylcarbamoyl (e.g. methylcarbamoyl, ethylcarbamoyl, propylcarbamoyl, iso-propylcarbamoyl, butylcarbamoyl, hexylcarbamoyl, etc.), lower alkaroyl (e.g. formyl, acetyl, propionyl, butyryl, pentanoyl, hexanoyl, pivaloyl, etc.), etc.; protected amino such as acylamino, in which the acyl moiety may be the same as those exemplified below, preferably lower alkanoylamino (e.g. formylamino, acetylamino, propionylamino, butyrylamino, valerylamino, hexanoylamino, pivaloylamino, etc.); carboxy; protected carboxy such as esterified carboxy, for example lower alkoxycarbonyl (e.g. methoxycarbonyl, ethoxycarbonyl, propoxycarbonyl, iso-propoxycarbonyl, butoxycarbonyl, hexyloxycarbonyl, neopentyloxycarbonyl, etc.); ar(lower)alkyl such as mono or di or triphenyl(lower)alkyl (e.g. benzyl, benzhydryl, trityl, phenethyl, etc.); and the like.

Preferred embodiments of the definitions for A, $R^1$, $R^2$, $R^3$ and $R^4$ are as follows.

A is lower alkylene, more preferably $C_1$-$C_4$alkylene (e.g. methylene, ethylene, dimethylmethylene, etc.);

$R^1$ and $R^2$ are each lower alkyloxy, more preferably $C_1$-$C_4$alkyloxy (e.g. methoxy, etc.);

$R^3$ is amino-protective group such as acyl, more preferably, lower alkanoyl (e.g. formyl, acetyl, propionyl, etc.); carboxy(lower)alkanoyl (e.g. carboxyacetyl, 3-carboxypropionyl, etc.); protected carboxy(lower)alkanoyl, for example, esterified carboxy(lower)alkanoyl such as lower alkoxycarbonyl(lower)alkanoyl (e.g. ethoxycarbonylacetyl, 3-ethoxycarbonylpropionyl, etc.); lower alkylthio(lower)alkanoyl [e.g. (methylthio)acetyl, etc.]; carbamoyl; lower alkylcarbamoyl (e.g. methylcarbamoyl, ethylcarbamoyl, isopropylcarbamoy, etc.); 5 or 6-membered aliphatic heteromonocyclic carbonyl having one nitrogen atom and one additional hetero atom selected from oxygen and sulfur such as morpholinylcarbonyl (e.g. morpholinocarbonyl, etc.), thiazolidinylcarbonyl (e.g. thiazolidin-4-ylcarbonyl, etc.), etc.; 5 or 6-membered unsaturated heteromonocyclic carbonyl having one or two nitrogen atom(s) which may be substituted by one or two substituent(s) selected from lower alkyl and oxo such as pyridylcarbonyl (e.g. 3-pyridylcarbonyl, etc.), di or tetrahydropyridazinylcarbonyl substituted by oxo or oxo and lower alkyl [e.g. (2,3-dihydro-6-methyl-3-oxopyridazin-4-yl)carbonyl, 1,4,5,6-tetrahydro-6-oxopyridazin-3-yl)carbonyl, etc.], etc.; 9 or 10-membered aromatic heterobicyclic carbonyl having three nitrogen atoms such as imidazopyridylcarbonyl [e.g. (imidazo[4,5-c]pyridin-2-yl)carbonyl, etc.); arylthio(lower)alkanoyl such as $C_6$-$C_{10}$aryl(lower)-alkanoyl [e.g. [phenylthio)acetyl, etc.]; 5 or 6-membered aromatic heteromonocyclic (lower)-alkanoyl, in which the heterocyclic moiety has one nitrogen atom or nitrogen atom and one sulfur atom and further is optionally substituted by amino such as pyridyl(lower)alkanoyl (e.g. 3-pyridylacetyl, etc.), aminothiazolyl(lower)alkanoyl (e.g. 2-aminothiazol-4-ylacetyl, etc.), etc.; 5 or 6-membered aliphatic heteromonocyclic (lower)alkanoyl, in which the heterocyclic moiety has one nitrogen atom and one sulfur atom and further is substituted by one to three oxo group(s) such as thiazolidinyl substituted by three oxo group [e.g. (1,1,4-trioxothiazolidin-3-yl)acetyl, etc.]; 9 or 10-membered aromatic heterobicyclic (lower)-alkanoyl in which the heterocyclic moiety has three nitrogen atoms and further is substituted by lower alkyl such as lower alkylimidazopyridyl(lower)-alkanoyl [e.g. (7-methylimidazo[1,2-a]pyridin-2-yl)-acetyl, etc.]; arenesulfonylamino(lower)alkanoyl such as $C_6$-$C_1$-0arenesulfonylamino(lower)alkanoyl (e.g. p-toluenesulfonylglycyl, etc.); and 5 or 6-membered aromatic heteromonocyclic (lower)alkenoyl, in which the heterocyclic moiety has one nitrogen atom such as pyridyl(lower)alkenoyl [e.g. 2-(3-pyridyl)acryloyl, etc.]; and
$R^4$ is hydrogen.

The processes for preparing the object compound (I) are explained in detail in the following.

Process (a)

The object compound (I) or a salt thereof can be prepared by reacting the compound (II) with the compound (III) or a salt thereof.

Suitable salt of the compound (III) can be referred to the ones as exemplified for the compound (I).

The reaction is usually carried out in a conventional solvent such as water, alcohol (e.g., methanol, ethanol, iso-propyl alcohol, etc.), tetrahydrofuran, dioxane, chloroform, methylene chloride, dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to heating.

The reaction may be also carried out in the presence of an inorganic or an organic base such as an alkali metal hydroxide, an alkali metal bicarbonate, alkali metal carbonte, alkali metal acetate, tri(lower)alkylamine, pyridine, N-(lower)alkylmorpholine, N,N-di(lower)-alkylbenzylamine, N,N-di(lower)alkylaniline or the like. When the base is in liquid, it can be used also as a solvent.

Process (b)

The object compound (I) or a salt thereof can be prepared by subjecting the compound (IV) or a salt thereof to an introduction of an amino-protective group.

This reaction is carried out in a conventional manner under the existence of a suitable amino-protective group introducing agent which is capable of converting an amino moiety to an protected amino moiety.

The amino-protective group introduced by the amino-protective group introducing agent can be referred to one explained before.

Suitable amino-protective group introducing agent may be carboxylic, carbonic, sulfonic and carbamic acid and their reactive derivative such as acid halide (e.g. acid chloride, etc.), acid anhydride; activated ester; substituted isocyanate, for example N-(lower)alkylisocyanate (e.g. methylisocyanate, ethylisocyanate N-isopropylisocyanate, etc.), and the like.

The reaction is usually carried out in a conventional solvent such as alcohol (e.g., methanol, ethanol, iso-propyl alcohol, etc.), tetrahydrofuran, dioxane, dichloromethane, chloroform, dimethyl acetamide, N,N-dimethylformamide or any other organic solvent which does not adversely influence the reaction.

The reaction temperature is not critical and the reaction is usually carried out under cooling to warming.

Process (c)

The compound (Ib) or a salt thereof can be prepared by subjecting the compound (Ia) or a salt thereof to elimination reaction of the carboxy-protective group on $R_a^3$.

Suitable method for this elimination reaction may include conventional one such as hydrolysis.

Hydrolysis is preferably carried out in the presence of an acid or a base.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

The acid suitable for this hydrolysis can be selected according to the kinds of the carboxy-protective group to be eliminated, for example, this hydrolysis can preferably be applied to the carboxy-protective group for $R_a^3$ such as lower alkoxycarbonyl or lower alkanoyl.

Suitable base may include an inorganic base and an organic base such as an alkali metal (e.g. sodium, potassium, etc.), an alkaline earth metal (e.g. magnesium, calcium, etc.), the hydroxide or carbonate or hydrogencarbonate thereof, trialkylamine (e.g. trimethylamine, triethylamine, etc.), picoline, 1,5-diazabicyclo[4.3.0]-none-5-ene, 1,4-diazabicyclo[2.2.2]octane, 1,8-diazabicyclo[5.4.0]undecene-7, or the like.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to heating.

The object compounds (I), (Ia) and (Ib) obtained by the above processes or salts thereof can be isolated and purified by using conventional manners in this field, such as column chromatography, recrystallization, or the like.

The compound (I) may be converted into the aforesaid salts according to a conventional manner.

Some of the starting compound (IV) in Process (b) are novel and can be prepared by the following process.

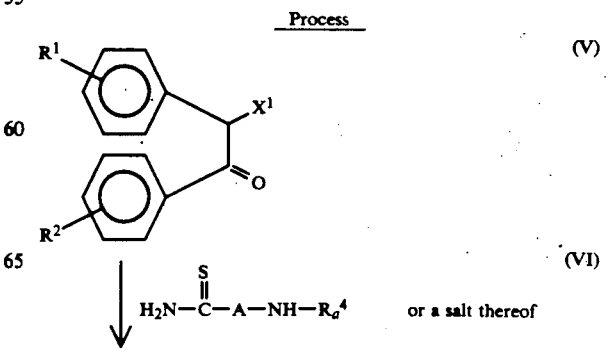

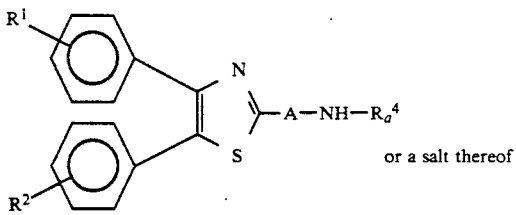

(IVa) or a salt thereof wherein

A, $R^1$ and $R^2$ are each as defined above, $R_a^4$ is hydrogen, lower alkyl which may have heterocyclic group, piperidyl which may have suitable substituent(s) or amidino, and $X^1$ is an acid residue.

Process for the preparation of the starting compound (IVa) is explained in detail in the following.

Process

The compound (IVa) or a salt thereof can be prepared by reacting the compound (V) with the compound (VI) or a salt thereof.

Suitable salt of the compound (VI) can be referred to the ones as exemplified for the compound (I).

This reaction can be carried out in a similar manner to that of the aforementioned Process (a), and therefore the reaction conditions (e.g. base, solvent, temperature, etc.) can be referred to those of Process (a).

The other starting compounds can be prepared in a conventional manner.

The new thiazole compounds (I) and a pharmaceutically acceptable salt thereof of the present invention possess strong antithrombotic activity inhibiting the activities against cyclooxygenase, thrombin, phosphodiesterase and the like, and/or inhibiting aggregation of platelet; vasodilating activity; anti-allergic activity; anti-inflammatory activity; and 5-lipoxygenase inhibitory activity; particularly antithrombotic activity, and therefore are useful as antithrombotic agent, vasodilating agent, anti-allergic agent, anti-inflammatory agent and 5-lipoxygenase inhibiting agent, particularly antithrombotic agent.

Accordingly, the new thiazole compounds (I) and a pharmaceutically acceptable salt thereof can be used for prophylactic and therapeutic treatment of cerebral thrombosis, atrophic thrombosis; coronary thrombosis; creeping thrombosis; dialation thrombosis; jumping thrombosis; mural thrombosis; placental thrombosis; platelet thrombosis; posttraumatic arterial thrombosis; thrombostasis; compression thrombosis; peripheral vascular disorders such as chronic arterial occlusion; transient ischemic attack; myocardial infarction; cerebral infarction; reocclusion after percutaneous transluminal coronary angioplasty or percutaneous transluminal coronary recanalization; arteriosclerosis; cerebiral vasospam; disseminated intravascular coagulopathy; hypertension such as pulmonary hypertension; asthma; psoriasis; hepatitis; pancreatitis; arthritis; nephritis; inflammatory bowel diseases; septic shock; rhinitis; conjunctivitis; epidermitis; rheumatism; peptic ulcer; gout; dysmnesia; senile dementia; Crohn's disease; adult respiratory disease syndrome; endotoxin shock; and the like.

And, these compounds are also useful for inhibition of thrombosis during extracorporeal circulation such as dialysis.

Further, these compounds are also expected to have antipyretic activity, analgesic activity, antiviral activity, antifungal activity, and the like.

The thiazole compounds (I) and a pharmaceutically acceptable salt thereof scarcely have side effect exerting a bad influence upon patients.

In order to show the utilities of the thiazole compounds (I) and a pharmaceutically acceptable salt thereof of the present invention, pharmacological test data of the representative compound of the thiazole compounds (I) are illustrated in the following.

The expressions of "Example 1", "Example 15", "Example 19" and "Example 24", in the following tests mean the compounds prepared in Examples 1, 15, 19 and 24, respectively.

Platelet aggregation ex vivo

1. Test method

Male Hartley guinea-pigs weighing about 300 g were used after 24 hours fasting. Six hours after oral administration of the test compound or vehicle of test compound (control), blood was collected into a tube containing 0.1 vol. of 3.8% sodium citrate and prepared platelet rich plasma (PRP).

To the 250 $\mu$l of PRP, 5 $\mu$l of arachidonic acid (final 50 $\mu$M) was added as an aggregation inducer. Aggregation was measured by using an aggregometer (NKK HEMA-TRACER 1). The following result shows the relationship between the dose of the test compound and the percentage (%) of its inhibitory activity against the platelet aggregation responses.

2. Test result

| Test compound | Dose (mg/kg) | Inhibition (%) |
|---|---|---|
| Example 15 | 1.0 | 100 |

Relaxation effect on isolated rat aorta

1. Test method

Helical strip of rat thoracic aorta was suspended in the organ bath containing Tyrode solution gassed with 95% $O_2$–5% $CO_2$ at 37° C. under 0.5 g load. Contraction was induced by addition of KCl solution (final concentration was 30 mM). After the tonus reached plateau, drug solution (dissolved in dimethyl sulfoxide) was added cumulatively and finally $10^{-4}$M of papaverine was added to get maximum relaxation. Activities of the test compound were expressed as $ED_{50}$ values i.e. doses required to relax the isolated rat aorta by 50%.

2. Test result

| Test compounds | $ED_{50}$ (M) |
|---|---|
| Example 15 | $7.3 \times 10^{-6}$ |
| Example 19 | $8.2 \times 10^{-6}$ |

Effect on malondialdehyde (MDA) production in rabbit platelets

1. Test method

Washed rabbit PRP (900 $\mu$l) was preincubated with drug solution (dissolved in dimethyl sulfoxide) (100 $\mu$l) at 37° C. for 5 minutes. Then, 2.5 mM arachidonic acid solution (20 $\mu$l) was added to the reaction mixture. After 3 minutes, thiobarbiturate reagent (1000 $\mu$l) was added, and the reaction mixture was heated in a boiled water. After centrifugation at 1500 g for 10 minutes, the absorbance of suparnatant was measured at 532 nm.

This test was carried out to see inhibitory activity of the test compound against the activity of cyclooxygenase. Activity of the test compound was expressed as $IC_{50}$ values i.e. doses required to inhibit the production of malondialdehyde by 50%.

2. Test result

| Test compound | $IC_{50}$ (M) |
|---|---|
| Example 1 | $1.5 \times 10^{-8}$ |

Assay for thrombin induced aggregation in human washed platelets

1. Test method

Blood was drawn from healthy volunteers into a plastic tube containing 1/10 volume of 3.8% sodium citrate and centrifuged at 120 g for 10 minutes to obtain platelet rich plasma (PRP). An equal volume of 25 mM Tris-HCl buffer (pH 7.4) containing 130 mM NaCl and 1.5 mM EDTA (buffer A) was added to the PRP, mixed and centrifuged at 1500 g for 10 minutes. The platelet pellet was suspended in buffer A and centrifuged at 1500 g for 5 minutes. The platelets were resuspended in 25 mM Tris-HCl buffer (pH 7.4) containing 130 mM NaCl and 0.3 mM EDTA and recentrifuged at 1500 g for 5 minutes. The platelets were finally suspended in Tyrode solution containing 0.3 % bovine serum albumin and the platelet count was adjusted to $3 \times 10^8$/ml. To 247.5 μl of platelet suspension, 2.5 μl of drug solution was added and incubated for 2 minutes at 37° C. prior to addition of thrombin solution (final conc. 0.3–0.5 U/ml). Platelet aggregation was turbidometrically measured using a HEMA-TRACER 1.

2. Test result

| Compound | Concentration (M) | Inhibition of the aggregation (%) |
|---|---|---|
| Example 24 | $1.0 \times 10^{-5}$ | 71.3 |

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.001 mg/kg to 500 mg/kg, preferably 0.01 mg/Kg to 10 mg/Kg, 1 to 4 times a day. However, the above dosage may be increased or decreased according to age, weight and conditions of the patient or the administering method.

The following preparations and examples are given only for the purpose of illustrating the present invention in more detail.

Preparation 1

2-tert-Butyloxycarbonylamino-2-methylpropiononitrile (80.00 g) in Benzene (700 ml) was stirred at 0° C., and saturated with hydrogen sulfide. To the reaction mixture was dropped triethyl amine (1000 ml) and bubbled hydrogen sulfide at ambient temperature for 9 hours, and left at the same temperature for 19 hours. The reaction mixture was added to water and extracted with ethyl acetate. The organic layer was washed with water, saturated aqueous sodium hydrogencarbonate, water and brine, and dried over magnesium sulfate. After filtration, the filtrate was evaporated in vacuo. The residue was washed with n-hexane, to give 2-tert-butyloxycarbonylamino-2-methylpropanethioamide (80.14 g).

mp 155°–157° C.

IR (Nujol) 3320, 3150, 1680, 1630, 1610, 1510 cm$^{-1}$

NMR (DMS-d$_6$, δ) : 1.37 (9H, s), 1.45 (6H, s), 6.98 (1H, s), 8.83 (1H, s), 9.57 (1H, s)

MASS (M/Z): 218 (M+)

Preparation 2

A mixture of 1,2-bis(4-methoxyphenyl)-2-chloroethanone (5.00 g) and 2-tert-butyloxycarbonylamino-2-methylpropanethioamide (4.50 g) in dimethylformamide (25 ml) was stirred at 70° C. for 6 hours. After allowing to cool to the ambient temperature, the reaction mixture was dropped into water. The precipitates were collected by filtration. The resulting residue (6.28 g) was dissolved with dichloromethane (120 ml), and stirred at 2° C. To the reaction mixture was added 1,4-dioxan solution of 4N hydrogen chloride (60 ml), and stirred at ambient temperature for 1 hour. The resulting residue was evaporated in vacuo. The residue was added iso-propyl ether (300 ml) and stirred at 2° C. for 3 hours. The resulting precipitate was collected by filtration and washed with iso-propyl ether, to give 2-(1-amino-1-methylethyl)-4,5-bis(4-methoxyphenyl)-thiazole hydrochloride (5.5 g).

mp: 97°–100° C.

IR (Nujol): 3250, 1610, 1510, 1250 cm$^{-1}$

NMR (DMSO-d$_6$, δ): 1.78 (6H, s), 3.75 (3H, s), 3.79 (3H, s), 6.92 (2H, d, J=9Hz), 6.99 (2H, d, J=9Hz), 7.28 (2H, d, J=9Hz), 7.44 (2H, d, J=9Hz), 8.95 (2H, s)

MASS (M/Z): 354 (M+ of free compound)

Preparation 3

2-(2-Aminoethyl)-4,5-bis(4-methoxyphenyl)thiazole hydrochloride was obtained according to a similar manner to that of Preparation 2.

mp 95°–100° C.

IR (Nujol) : 3400, 1610, 1510 cm$^{-1}$

NMR (DMSO-d$_6$, δ) : 3.26-3.35 (4H, m), 3.75 (3H, s), 3.78 (3H, s), 6.88 (2H, d, J=9Hz), 6.96 (2H, d, J=9Hz), 7.25 (2H, d, J=9Hz), 7.40 (2H, d, J=9Hz), 8.27 (3H, br s)

MASS (M/Z): 340 (M+ of free compound)

Example 1

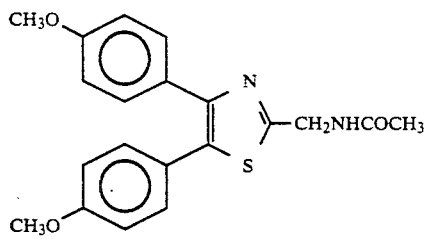

A mixture of 1,2-bis(4-methoxyphenyl)-2-chloroethanone (5.99 g) and 2-(acetylamino)ethanethioamide (3.00 g) in ethanol (30 ml) was refluxed for 2 hours. After allowing to cool to room temperature, the solvent was evaporated in vacuo, and the residue was dissolved in chloroform (200 ml) and aqueous solution of sodium hydrogencarbonate (200 ml). The separated organic layer was washed with water and brine, dried over magnesium sulfate and treated with activated charcoal. After filtration, the filtrate was evaporated in vacuo. The resulting residue was dissolved in diethyl ether, added ethanol solution of hydrogen chloride, and the resulting precipitate was collected by filtration. The resulting crude compound was recrystallized with ethanol 10 ml). And the resulting crystal was collected by filtration, washed with ethanol and diethyl ether, and dried to give 2-acetylaminomethyl-4,5-bis(4-methoxyphenyl)thiazole (2.52 g).

mp: 138°-141° C.

IR (Nujol): 3270 (br), 1750, 1650, 1610, 1520, 1510 cm$^{-1}$

NMR (DMSO-d$_6$, δ): 1.95 (3H, s), 3.74 (3H, s), 3.81 (3H, s), 4.53 (2H, d, J=6Hz), 6.90 (2H, d, J=7Hz), 6.95 (2H, d, J=7Hz), 7.25 (2H, d, J=8Hz), 7.40 (2H, d, J=8Hz), 8.80 (1H, t, J=6Hz)

MASS (M/Z) : 368 (M+)

The following compounds were obtained by reacting 1,2-bis(4-methoxyphenyl)-2-chloroethanone with the corresponding thioamide derivatives according to a similar manner to that of Example 1.

Example 2

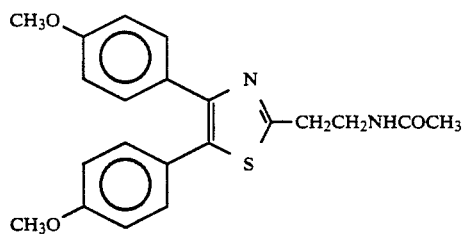

2-(2-Acetylaminoethyl)-4,5-bis(4-methoxyphenyl)-thiazole mp: 83°-86° C.

IR (Nujol): 3300, 1640, 1605, 1550, 1535, 1510, 1500 cm$^{-1}$

NMR (DMS-d$_6$, δ): 1.83 (3H, s), 3.10 (2H, t, J=7.0Hz), 3.45 (2H, t, d, J=7.0Hz, 5Hz), 3.74 (3H, s), 3.77 (3H, s), 6.87 (2H, d, J=8.9Hz), 6.95 (2H, d, J=8.9Hz), 7.23 (2H, d, J=8.9Hz), 7.38 (2H, d, J=8.9Hz), 8.09 (1H, t, J=5Hz)

MASS (M/Z): 382 (M+)

Example 3

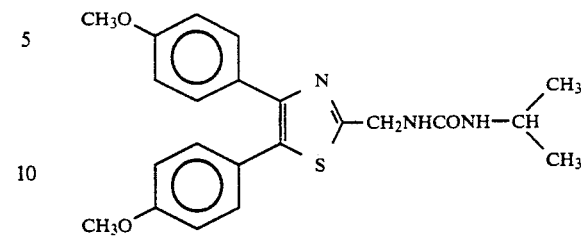

4,5-Bis(4-methoxyphenyl)-2-(3-isopropylureidomethyl)thiazole mp : 152°-154° C.

IR (Nujol): 3335, 1630, 1610, 1580, 1520 cm$^{-1}$

NMR (DMSO-d$_6$, δ): 1.06 (6H, d, J=6.5Hz), 3.4-3 6 (1H, m), 3.74 (3H, s), 3.77 (3H, s), 4.50 (2H, d, J=5.5Hz), 6.09 (1H, d, J=7.8Hz), 6 63 (1H, t, J=5.5Hz), 6.86 (2H, d, J=8.8Hz), 6.93 (2H, d, J=8.8Hz), 7.23 (2H, d, J=8.8Hz), 7.38 (2H, d, J=8.8Hz)

Example 4

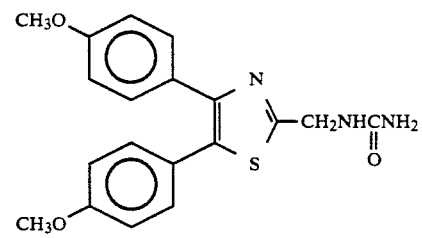

4,5-Bis(4-methoxyphenyl)-2-(ureidomethyl)thiazole mp: 149°-150° C.

IR (Nujol): 3250, 1660, 1600, 1510 cm$^{-1}$

NMR (DMS-d$_6$, δ) : 3.74 (3H, s), 3.77 (3H, s), 4.45 (2H, d, J=6Hz), 5.78 (2H, s), 6.83-6.89 (3H, m), 6.94 (2H, d, J=9Hz), 7.23 (2H, d, J=9Hz), 7.36 (2H, d, J=9Hz)

MASS (M/Z): 369 (M+)

Example 5

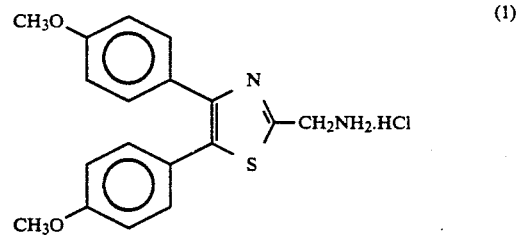

(1)

A mixture of 2-acetylaminomethyl-4,5-4-methoxyphenyl)thiazole (1.80 g) and concentrated hydrochloric acid (10 ml) was refluxed for 50 minutes. After allowing to cool to ambient temperature, the mixture was poured into water. The resulting solution was neutralized by addition of 4N sodium hydroxide and extracted with ethyl acetate. The organic layer was washed with saturated sodium hydrogencarbonate solution, water and brine, and dried over magnesium sulfate and treated with activated charcoal. After filtration, the filtrate was evaporated in vacuo, and the resulting residue was dissolved in ethanol and added ethanol solution of hydrogen chloride.

The resulting mixture was added diethyl ether and triturated to give a powder.

This powder was washed with ethanol and diethyl ether to give 2-aminomethyl-4,5-bis(4-methoxyphenyl)-thiazole hydrochloride (0.96 g).

mp: 141°-144° C.

IR (Nujol): 3350 (br), 1600, 1535, 1505 cm$^{-1}$

NMR (DMSO-d$_6$, δ): 3.75 (3H, s), 3.79 (3H, s), 4.44 (2H, s), 6.90 (2H, d, J=9Hz), 6.98 (2H, d, J=9Hz), 7.27 (2H, d, J=9Hz), 7.43 (2H, d, J=9Hz)

MASS (M/Z): 326 (M+)

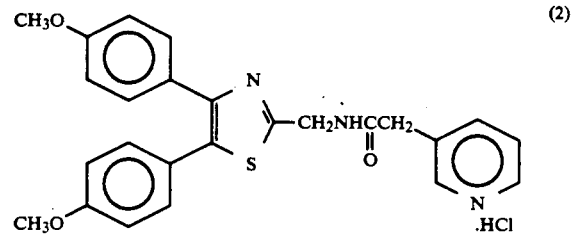

(2)

2-Aminomethyl-4,5-bis(4-methoxyphenyl)thiazole hydrochloride (1.00 g) was added to a mixture of dichloromethane and saturated aqueous solution of sodium hydrogencarbonate, and was extracted with dichloromethane. The organic layer was washed with water, and brine, and dried over magnesium sulfate. After filtration, the filtrate was evaporated in vacuo, and resulting residue was dissolved in dimethylformamide (25 ml). To the resulting mixture was added 1-(3-dimethylaminopropyl)-3ethylcarbodiimide hydrochloride (0.64 g) and 3-pyridylacetic acid hydrochloride (0.52 g), and stirred at ambient temperature for 2 hours and stirred at 60° C. for 5 hours. After allowing to cool to ambient temperature, the mixture was poured into water, and extracted with ethyl acetate. The organic layer was washed with saturated aqueous solution of sodium hydrogencarbonate, water, and brine, and dried over magnesium sulfate and treated with activated charcoal. After filtration, the filtrate was evaporated in vacuo. The residue was subjected to column chromatography on silica gel (50 g) and eluted with a mixture of methanol and chloroform. The fractions containing the object compound were combined and evaporated in vacuo, and the resulting residue was dissolved in ethanol, and added an ethanol solution of hydrogen chloride. The mixture was evaporated in vacuo, and the resulting precipitate was collected by filtration and washed with diethyl ether, to give 4,5-bis(4-methoxyphenyl)-2-(3-pyridylacetylaminomethyl)-thiazole hydrochloride (0.52 g).

mp: 97°-100° C.

IR (CH$_2$Cl$_2$): 1680, 1610, 1520, 1170 cm$^{-1}$

NMR (DMSO-d$_6$, δ): 3.75 (3H, s), 3.78 (3H, s), 3.90 (2H, s), 4.59 (2H, d, J=6Hz), 6.88 (2H, d, J=9Hz), 6.95 (2H, d, J=9Hz), 7.22 (2H, d, J=9Hz), 7.35 (2H, d, J=9Hz), 8.04 (1H, dd, J=6Hz, 8Hz), 8.52 (1H, d, J=8Hz), 8.85 (1H, d, J=6Hz), 8.89 (1H, s), 9.30 (1H, t, J=6Hz)

MASS (M/Z): 445 (M+ of free compound)

Example 6

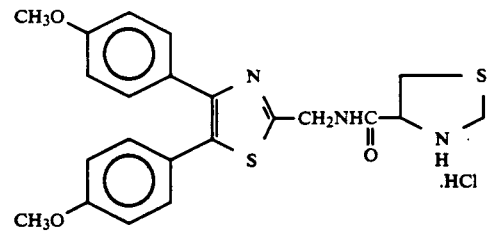

2-Aminomethyl-4,5-bis(4-methoxyphenyl)thiazole hydrochloride (1.20 g) was added to a mixture of dichloromethane and saturated aqueous sodium hydrogencarbonate, and was extracted with dichloromethane. The separated organic layer was washed with water, and brine, and dried over magnesium sulfate. After filtration, the filtrate was evaporated in vacuo, and resulting residue was dissolved in dimethylformamide (25 ml). To the reaction mixture was added 1-(3-dimethylaminopropyl)-3-ethylcarbodiimide hydrochloride (0.71 g) and 3-(tert-butyloxycarbonyl)-4-thiazolidinylcarboxylic acid (0.77 g), and stirred at ambient temperature for 2 hours. The mixture was poured into water, and extracted with ethyl acetate. The separated organic layer was washed with saturated aqueous sodium hydrogencarbonate, water, and brine, and dried over magnesium sulfate and treated with activated charcoal. After filtration, the filtrate was evaporated in vacuo. The residue was subjected to column chromatography on silica gel (50 g) and eluted with a mixture of methanol and chloroform. The fractions containing the object compound were combined and evaporated in vacuo. The resulting residue (oil-compound) (1.10 g) was dissolved with dichloromethane (20 ml), and stirred at 2° C. To the reaction mixture was added 1,4-dioxan solution of 4N hydrogen chloride (10 ml), and stirred at ambient temperature for 1 hour. The resulting residue was evaporated in vacuo. The residue was added isopropyl ether (50 ml) and stirred at 2° C. for 3 hours. The resulting precipitate was collected by filtration and washed with iso-propyl ether, to give 4-methoxyphenyl)-2-(4-thiazolidinylcarbonylaminomethyl)-thiazole hydrochloride (0.45 g).

mp: 117°-119° C.

IR (Nujol): 3350, 3180, 1680, 1610, 1520 cm$^{-1}$

NMR (DMSO-d$_6$, δ): 3.75 (3H, s), 3.77 (3H, s), 4.22 (2H, d, J=6Hz), 4.33-4.56 (6H, m), 6.88 (2H, d, J=9Hz), 6.96 (2H, d, J=9Hz), 7.24 (2H, d, J=9Hz), 7.37 (2H, d, J=9Hz), 9.78 (1H, t, J=6Hz)

MASS (M/Z): 441 (M+ of free compound)

The following compounds were obtained by reacting 2-aminomethyl-4,5-bis(4-methoxyphenyl)thiazole hydrochloride with the corresponding carboxylic acid derivatives according to a similar manner to that of Example 5-(2).

Example 7

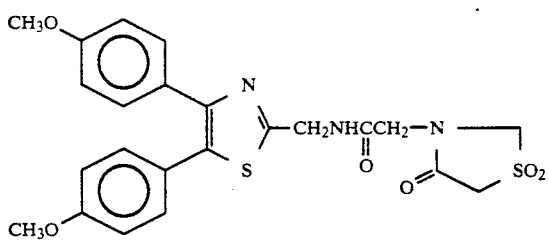

4,5-Bis(4-methoxyphenyl)-2-{(1,1,4-trioxo-3thiazolidinyl)acetylaminomethyl}thiazole
mp: 93°-95° C.
IR (Nujol): 3310 (br), 1700, 1680, 1600, 1510, 1330 cm$^{-1}$
NMR (DMSO-d$_6$, δ): 3.74 (3H, s), 3.77 (3H, s), 4.22 (4H, s), 4.60 (2H, d, J=6Hz), 4.83 (2H, s), 6.88 (2H, d, J=9Hz), 6.95 (2H, d, J=9Hz), 7.24 (2H, d, J=9Hz), 7.37 (2H, d, J=9Hz), 9.05 (1H, t, J=6Hz)
MASS (M/Z): 501 (M$^+$)

Example 8

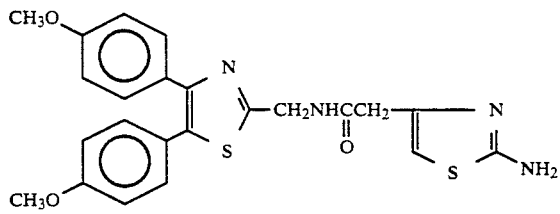

2-{(2-Amino-4-thiazolyl)acetylaminomethyl}-4,5-bis(4-methoxyphenyl)thiazole
mp: 70°-72° C.
IR (Nujol): 3290, 1660, 1610, 1510 cm$^{-1}$
NMR (DMSO-d$_6$, δ): 3.36 (2H, s), 3.74 (3H, s), 3.77 (3H, s), 4.55 (2H, d, J=6Hz), 6.30 (1H, s), 6.87 (2H, d, J=9Hz), 6.89 (2H, s), 6.95 (2H, d, J=9Hz), 7.23 (2H, d, J=9Hz), 7.36 (2H, d, J=9Hz), 8.78 (1H, t, J=6Hz)
MASS (M/Z): 466 (M$^+$)

Example 9

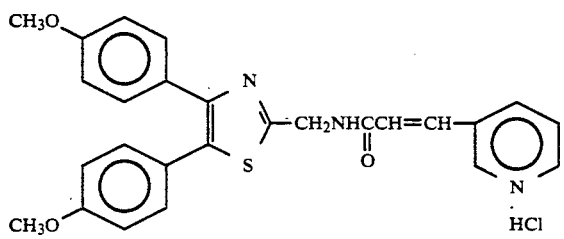

4,5-Bis(4-methoxyphenyl)-2-{3-(3-pyridyl)acryloylaminomethyl}thiazole hydrochloride
mp: 125°-127° C.
IR (CH$_2$Cl$_2$): 1680, 1610, 1520 cm$^{-1}$
NMR (DMSO-d$_6$, δ): 3.75 (3H, s), 3.77 (3H, s), 4.71 (2H, d, J=6Hz), 6.88 (2H, d, J=9Hz), 6.94 (2H, d, J=9Hz), 7.00 (1H, d, J=16Hz), 7.24 (2H, d, J=9Hz), 7.37 (2H, d, J=9Hz), 7.67 (1H, d, J=16Hz), 7.94 (1H, dd, J=4Hz, 8Hz), 8.60 (1H, d, J=8Hz), 8.82 (1H, , J=4Hz), 9.09 (1H, s), 9.30 (1H, t, J=6Hz)
MASS (M/Z): 457 (M$^+$ of free compound)

Example 10

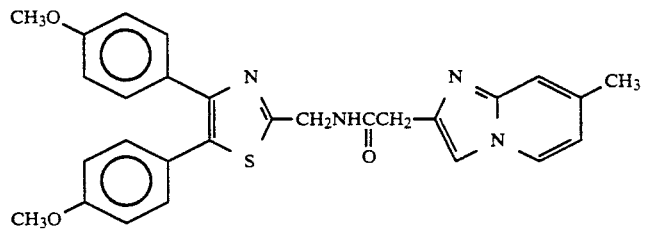

4,5-Bis(4-methoxyphenyl)-2-{(7-methylimidazo[1,2-a]pyridin-2-yl)acetylaminomethyl}thiazole
mp: 148°-150° C.
IR (Nujol): 3180, 1670, 1610, 1510 cm$^{-1}$
NMR (DMSO-d$_6$, δ): 2.33 (3H, s), 3.64 (2H, s), 3.74 (3H, s), 3.77 (3H, s), 4.57 (2H, d, J=6Hz), 6.69 (1H, d, J=7Hz), 6.86 (2H, d, J=9Hz), 6.94 (2H, d, J=9Hz), 7.20 (2H, d, J=9Hz), 7.24 (1H, s), 7.35 (2H, d, J=9Hz), 7.72 (1H, s), 8.37 (1H, d, J=7Hz), 8.91 (1H, t, J=6Hz)
MASS (M/Z): 498 (M$^+$)

Example 11

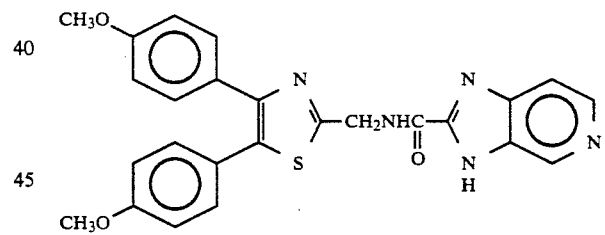

4,5-Bis(4-methoxyphenyl)-2-{(imidazo[4,5-c]pyridin-2-yl]carbonylaminomethyl}thiazole
mp: 140°-145° C.
IR (Nujol): 3400, 3200, 1680, 1610, 1550 cm$^{-1}$
NMR (DMSO-d$_6$, δ): 3.75 (6H, s), 4.79 (2H, d, J=5Hz), 6.79 (2H, d, J=9Hz), 6.90 (2H, d, J=9Hz), 7.17 (2H, d, J=9Hz), 7.32 (2H, d, J=9Hz), 7.55 (1H, d, J=6Hz), 8.35 (1H, d, J=6Hz), 8.98 (1H, s)

Example 12

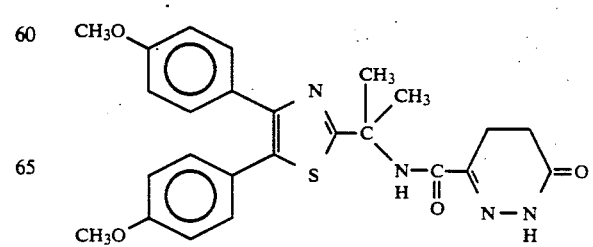

4,5-Bis(4-methoxyphenyl)-2-{1-methyl-1-[(6-oxo-1,4,5,6-tetrahyjdropyridazin-3-yl)carbonylamino]ethyl}-thiazole mp: 163°–165° C.

IR (Nujol): 3350, 1680, 1600, 1510, 1490 cm$^{-1}$

NMR (DMSO-d$_6$, δ): 1.77 (6H, s), 2.40 (2H, t, J=8Hz), 2.71 (2H, t, J=8Hz), 3.75 (3H, s), 3.77 (3H, s), 6.89 (3H, d, J=9Hz), 6.94 (3H, d, J=9Hz), 7.24 (3H, d, J=9Hz), 7.38 (3H, d, J=9Hz), 8.33 (1H, s), 11.14 (1H, s)

MASS (M/Z): 478 (M+)

Example 13

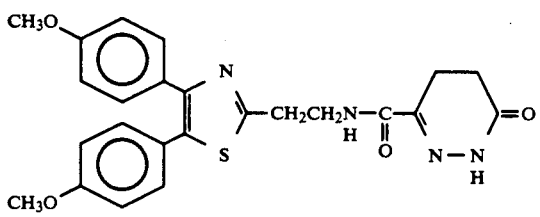

4,5-Bis(4-methoxyphenyl)-2-{2-[(6-oxo-1,4,5,6-tetrahydropyridazin-3-yl)carbonylamino]ethyl}thiazole mp: 186°–189° C.

IR (Nujol): 3400, 3200, 1680, 1660, 1520 cm$^{-1}$

NMR (DMSO$_6$, δ): 2.38 (2H, t, J=8Hz), 2.74 (2H, t, J=8Hz), 3.20 (2H, t, J=7Hz), 3.59 (2H, q, J=7.5Hz), 3.74 (3H, s), 3.77 (3H, s), 6.88 (2H, d, J=9Hz), 6.95 (2H, d, J=9Hz), 7.24 (2H, d, J=9Hz), 7.37 (2H, d, J=9Hz), 8.37 (1H, t, J=7Hz), 11.13 (1H, s)

Example 14

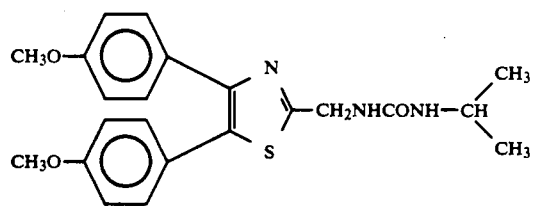

2-Aminomethyl-4,5-bis(4-methoxyphenyl)thiazole hydrochloride (1.00 g) was added to a mixture of dichloromethane and saturated aqueous sodium hydrogencarbonate, and 2-aminomethyl-4,5-bis(4-methoxyphenyl)thiazole was extracted with dichloromethane. The separated organic layer was washed with water and brine, and dried over magnesium sulfate. After filtration, the filtrate was evaporated in vacuo and the resulting residue was dissolved with tetrahydrofuran (20 ml) and methanol (7 ml). N-Isopropyl isocyanate (0.38 ml) was added thereto, and the reaction mixture was stirred at ambient temperature for 90 minutes. The reaction mixture was evaporated in vacuo, and the resulting powder was triturated with isopropyl ether, to give 4,5-bis(4-methoxyphenyl)-2-(3-isopropylureidomethyl)thiazole (1.04 g).

mp: 146°–149° C.

IR (Nujol): 3335, 1625, 1610, 1570, 1510 cm$^{-1}$

NMR (DMSO-d$_6$, δ): 1.06 (6H, d, J=6.5Hz), 3.74 (3H, s), 3.77 (3H, s), 3.70–3.85 (1H, m), 4.48 (2H, d, J=5.5Hz), 6.07 (1H, m), 6.61 (1H, m), 6.90 (2H, d, J=9Hz), 6.95 (2H, d, J=9Hz), 7.25 (2H, d, J=9Hz), 7.38 (2H, d, J=9Hz)

MASS (M/Z): 410 (M+-1)

Example 15

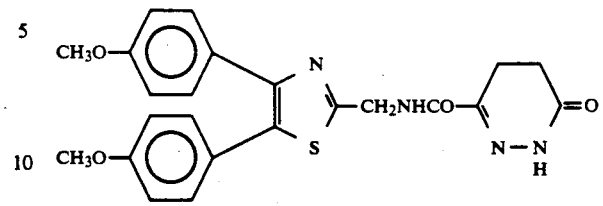

2-Aminomethyl-4,5-bis(4-methoxyphenyl)thiazole (0.80 g), which was obtained according to a similar manner to that of Example 14, was dissolved with N,N-dimethylformamide (10 ml). 1-Ethyl-3-3-dimethylaminopropyl)-carbodiimide hydrochloride (0.52 g) and 3-carboxy-6-oxo-1,4,5,6-tetrahydropyridazine (0.39 g) were added thereto, and the reaction mixture was stirred at ambient temperature for 3 hours and stirred at 50° C. for 7 hours and 30 minutes. After allowing to cool to room temperature, the mixture was poured into water, and extracted with ethyl acetate. The separated organic layer was washed with water and brine, and dried over magnesium sulfate and treated with activated charcoal. After filtration, the filtrate was evaporated in vacuo, and the resulting residue was triturated with isopropyl ether, ethanol and diethyl ether, to give 4,5-bis(4-methoxyphenyl)-2-{(6-oxo-1,4,5,6-tetrahydropyridazin-3-yl)carbonylaminomethyl}thiazole (0.49 g).

mp: 174°–175° C.

IR (Nujol): 3400, 3350, 3220, 3150, 1690, 1660, 1605, 1515 cm$^{-1}$

NMR (DMSO-d$_6$, δ): 2.42 (2H, t, J=8.2Hz), 2.78 (2H, t, J=8.2Hz), 3.74 (3H, s), 3.77 (3H, s), 4.64 (2H, d, J=6Hz), 6.87 (2H, d, J=8.8Hz), 6.93 (2H, d, J=8.8Hz), 7.23 (2H, d, J=8.8Hz), 7.37 (2H, d, J=8.8Hz), 9.03 (1H, t, J=6Hz), 11.2 (1H, s)

MASS (M/Z): 450 (M+)

The following compounds were obtained by reacting 2-aminomethyl-4,5-bis(4-methoxyphenyl)thiazole hydrochloride with the corresponding carboxylic acid derivatives according to a similar manner to that of Example 15.

Example 16

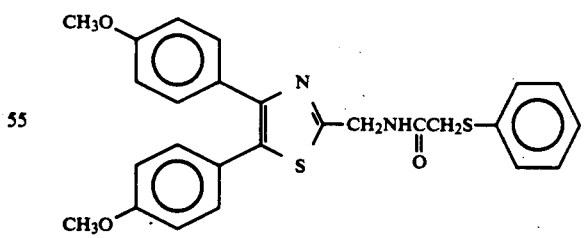

4,5-Bis(4-methoxyphenyl)-2-(phenylthioacethylaminomethyl)thiazole mp: 132°–133° C.

IR (Nujol): 3300, 1650, 1610, 1550, 1520, 1500 cm$^{-1}$

NMR (DMSO-d$_6$, δ): 3.74 (2H, s), 3.78 (6H, z), 4.56 (2H, d, J=6Hz), 6.86 (2H, d, J=8Hz), 6.91 (2H, d, J=8Hz), 7.17–7.40 (9H, m), 9.06 (1H, t, J=6Hz)

MASS (M/Z): 476

Example 17

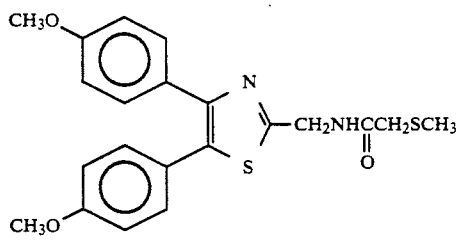

4,5-Bis(4-methoxyphenyl)-2-(methylthioacetylaminomethyl)thiazole
mp: 74°–75° C.
IR (Nujol): 3260, 1640, 1610, 1540, 1510 cm$^{-1}$
NMR (DMSO-d$_6$, δ): 2.15 (3H, s), 3.18 (2H, s), 3.74 (3H, s), 3.77 (3H, s), 4.60 (2H, d, J=6Hz), 6.87 (2H, d, J=8Hz), 6.95 (2H, d, J=8Hz), 7.23 (2H, d, J=8Hz), 7.37 (2H, d, J=8Hz), 8.92 (1H, t, J=6Hz)
MASS (M/Z): 414 (M+)

Example 18

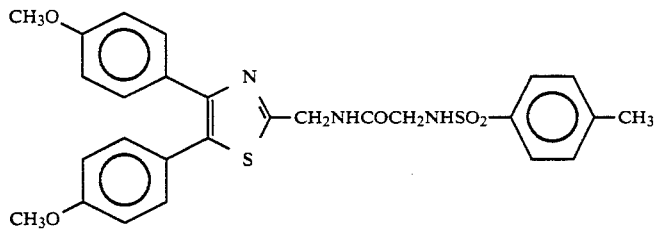

4,5-Bis(4-methoxyphenyl)-2-{N-[N-(p-toluenesulfonyl)-glycyl]aminomethyl}thiazole
mp: 65°–71° C.
IR (Nujol): 3250, 1665, 1615, 1580, 1510, 1500 cm$^{-1}$
NMR (DMSO-d$_6$, δ): 2.34 (3H, s), 3.49 (2H, d, J=5Hz), 3.74 (3H, s), 3.77 (3H, s), 4.52 (2H, d, J=6Hz), 6.77 (2H, d, J=9Hz), 6.87 (2H, d, J=9Hz), 7.11 (2H, d, J=9Hz), 7.30–7.50 (4H, m), 7.70 (2H, d, J=8Hz), 8.01 (1H, m), 8.83 (1H, t, J=6Hz)
MASS (M/Z): 537 (M+)

Example 19

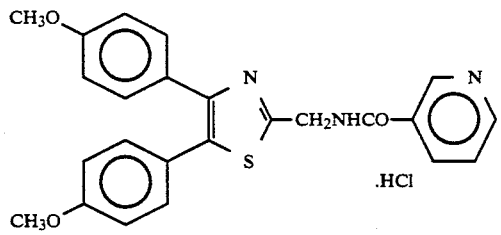

A mixture of 2-acetylaminomethyl-4,5-bis(4-methoxyphenyl)thiazole (1.00 g) and concentrated hydrochloric acid (7 ml) was refluxed for 2 hours and 40 minutes. After allowing to cool to ambient temperature, the mixture was poured into water, and the resulting solution was neutralized by addition of 4N sodium hydroxide, and extracted with ethyl acetate. The organic layer was washed with saturated sodium hydrogencarbonate solution, water, and brine, and dried over magnesium sulfate and treated with activated charcoal. After filtration, the filtrate was evaporated in vacuo to give 2-aminomethyl-4,5-bis(4-methoxyphenyl)thiazole hydrochloride. And this compound was dissolved in dichloromethane (10 ml) and triethylamine (0.33 ml). To the above reaction mixture was added a solution of nicotinoyl chloride hydrochloride (0.58 g) and dichloromethane (5 ml) at ambient temperature, and was stirred at ambient temperature for 3 hours and refluxed for one and a half hour. After allowing to cool to ambient temperature, the mixture was poured into water, and the resulting solution was neutralized by addition of 4N sodium hydroxide, and extracted with dichloromethane. The organic layer was washed with saturated aqueous sodium hydrogencarbonate, water, and brine, and dried over magnesium sulfate and treated with activated charcoal. After filtration, the filtrate was evaporated in vacuo, and the resulting residue was dissolved in diethyl ether, and added methanol solution of hydrogen chloride. The resulting precipitate was collected by filtration and washed with ethanol and diethyl ether to give 4,5-bis(4-methoxyphenyl)-2-(nicotinoylaminomethyl)-thiazole hydrochloride (0.63 g).
mp: 135°–144° C.
IR (Nujol): 1675, 1635, 1610, 1570, 1520 cm$^{-1}$
NMR (DMSO-d$_6$, δ): 3.75 (3H, s), 3.77 (3H, s), 4.83 (2H, d, J=5.6Hz), 6.88 (2H, d, J=8.5Hz), 6.94 (2H, d, J=8.5Hz), 7.24 (2H, d, J=8.5Hz), 7.40 (2H, d, J=8.5Hz), 8.15 (1H, dd, J=8.1Hz, 5.6Hz), 9.02 (1H, d, J=8.1Hz), 9.08 (1H, d, J=5.6Hz), 9.43 (1H, s), 10.42 (1H, t, J=5.6Hz)
MASS (M/Z): 431 (M+)

The following compounds were obtained by reacting 2-aminomethyl-4,5-bis(4-methoxyphenyl)thiazole hydrochloride with the corresponding acyl chloride according to a similar manner to that of latter part of Example 19.

Example 20

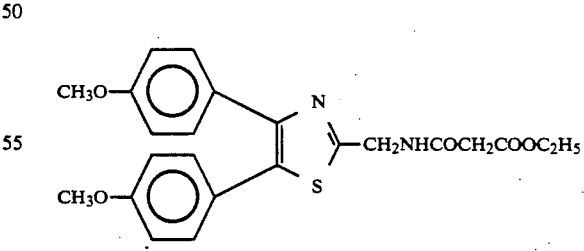

4,5-Bis(4-methoxyphenyl)-2-ethoxycarbonylacetylaminomethylthiazole
IR (Neat): 3300, 2980, 1735, 1660, 1610, 1535, 1510 cm$^{-1}$
NMR (DMSO-d$_6$, δ): 1.18 (3H, t, J=13Hz), 3.34 (2H, s), 3.74 (3H, s), 3.77 (3H, s), 4.08 (2H, q, J=13Hz), 4.58 (2H, d, J=5.9Hz), 6.87 (2H, d, J=8.8Hz), 6.95 (2H, d, J=8.8Hz), 7.23 (2H, d, J=8.8Hz), 7.36 (2H, d, J=8.8Hz), 9.03 (1H, t, J=5.9Hz)

MASS (M/Z): 440 (M+)

Example 21

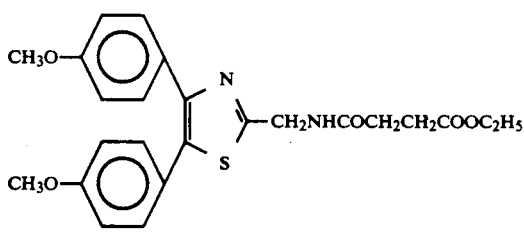

4,5-Bis(4-methoxyphenyl)-2-[(3-(ethoxycarbonyl)-propionyl}aminomethyl]thiazole

IR (Neat): 3300, 1730, 1660, 1605, 1535, 1510 cm$^{-1}$

NMR (DMSO-d$_6$, δ): 1.24 (3H, t, J=7.1Hz), 2.5-2.8 (4H, m), 3.80 (3H, s), 3.81 (3H, s), 4.14 (2H, q, J=7.1Hz), 4.73 (2H, d, J=5.7Hz), 6.63 (1H, m), 6.75-6.95 (4H, m), 7.25 (2H, d, J=8.8Hz), 7.43 (2H, d, J=8.8Hz)

MASS (M/Z): 454 (M+)

Example 22

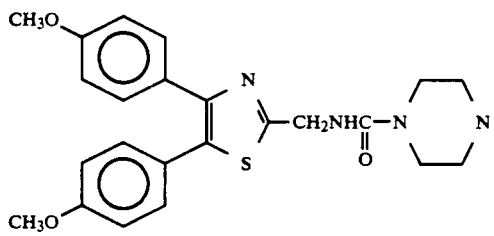

4,5-Bis(4-methoxyphenyl)-2-(morpholinocarbonylaminomethyl)thiazole mp: 127°-130° C.

IR (Nujol): 3300, 1630, 1610, 1550, 1540, 1520 cm$^{-1}$

NMR (DMSO-d$_6$, δ): 3.30-3.34 (8H, m), 3.74 (3H, s), 3.77 (3H, s), 4.50 (2H, d, J=6Hz), 6.87 (2H, d, J=8Hz), 6.94 (2H, d, J=8Hz), 7.23 (2H, d, J=8Hz), 7.36 (2H, d, J=8Hz), 7.55 (1H, t, J=6Hz)

MASS (M/Z): 439 (M+)

Example 23

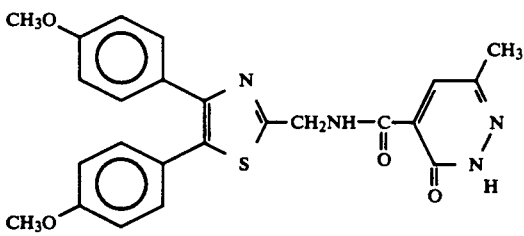

4,5-Bis(4-methoxyphenyl)-2-{(6-metnyl-3-oxo-2,3-dihydropyridazin-4-yl)carbonylaminomethyl}thiazole was obtained according to a similar manner to that of Example 6.

mp: 202°-204° C. (dec.)

IR (Nujol): 3220, 1670, 1630, 1605, 1510 cm$^{-1}$

NMR (DMSO-d$_6$, δ): 2.36 (3H, s), 3.75 (3H, s), 3.77 (3H, s), 4.86 (2H, d, J=6Hz), 6.74 (2H, d, J=9Hz), 6.87 (2H, d, J=9Hz), 7.23 (2H, d, J=9Hz), 7.38 (2H, d, J=9Hz), 8.06 (1H, s), 10.32 (1H, t, J=6Hz), 13.57 (1H, m)

The following compounds were obtained by reacting 2-aminomethyl-4,5-bis(4-methoxyphenyl)thiazole hydrochloride with the corresponding isocyanate derivatives according to a similar manner to that of Example 14.

Example 24

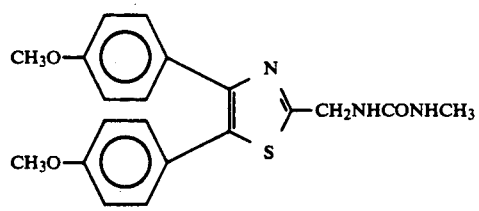

4,5-Bis(4-methoxyphenyl)-2-(3methylureidomethyl)-thiazole mp: 115°-118° C.

IR (Nujol): 3300, 1620, 1600, 1585, 1530, 1505 cm$^{-1}$

NMR (DMSO-d$_6$, δ): 2.60 (3H, s), 3.74 (3H, s), 3.77 (3H, s), 4.48 (2H, s), 6.87 (2H, d, J=8.8Hz), 6.93 (2H, d, J=8.8Hz), 7.23 (2H, d, J=8.8Hz), 7.36 (2H, d, J=8.8Hz)

MASS (M/Z): 383 (M+)

Example 25

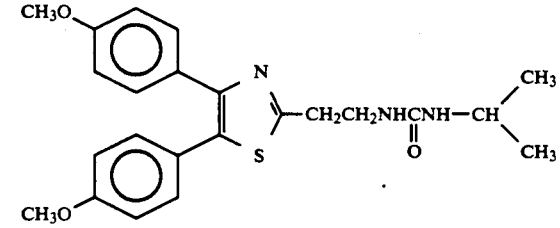

4,5-Bis(4-methoxyphenyl)-2-{2-(3-isopropylureido)-ethyl}thiazole mp: 129°-131° C.

IR (Nujol): 3310, 1620, 1510, 1460, 1300

NMR (DMSO-d$_6$, δ): 1.02 (6H, d, J=6Hz), 3.09 (2H, t, J=6Hz), 3.40 (2H, q, J=6Hz), 3.68 (1H, m), 3.75 (3H, s), 3.77 (3H, s), 5.85 (1H, d, J=8Hz), 5.93 (1H, t, J=6Hz), 6.92 (2H, d, J=9Hz), 7.38 (2H, d, J=9Hz)

MASS (M/Z): 425 (M+)

Example 26

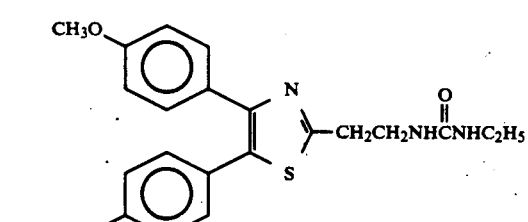

4,5-Bis(4-methoxyphenyl)-2-{2-(3-ethylureido)ethyl}-thiazole mp: 76°-77° C.

IR (Nujol): 3300, 1620, 1600, 1560, 1505 cm$^{-1}$

NMR (DMSO-d$_6$, δ): 0.98 (3H, t, J=7Hz), 2.95–3.10 (4H, m), 3.40 (2H, q, J=7Hz), 3.74 (3H, s), 3.77 (3H, s), 5.90–6.10 (2H, m), 6.87 (2H, d, J=9Hz), 6.95 (2H, d, J=9Hz), 7.23 (2H, d, J=9Hz), 7.38 (2H, d, J=9Hz)

MASS (M/Z): 411 (M+)

Example 27

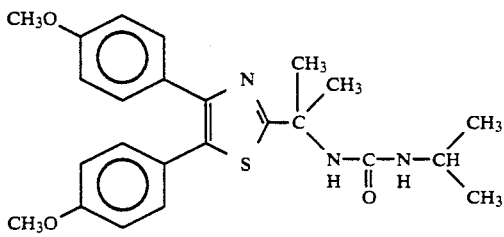

4,5-Bis(4-methoxyphenyl)-2-{[1-methyl-1-(3-isopropylureido)]ethyl}thiazole mp: 183°–184° C.

IR (Nujol): 3350, 1640, 1610, 1510 cm$^{-1}$

NMR (DMSO-d$_6$, δ): 1.02 (6H, d, J=6Hz), 1.64 (6H, s), 3.56–3.67 (1H, m), 3.74 (3H, s), 3.77 (3H, s), 5.79 (1H, d, J=8Hz), 6.47 (1H, s), 6.87 (2H, d, J=9Hz), 6.94 (2H, d, J=9Hz), 7.22 (2H, d, J=9Hz), 7.37 (2H, d, J=9Hz)

MASS (M/Z): 439 (M+)

Example 28

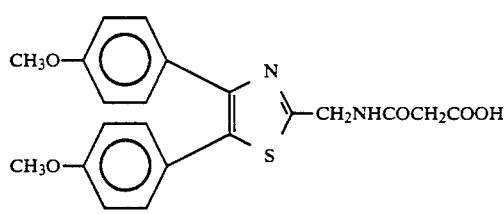

A mixture of 4,5-bis(4methoxyphenyl)-2-ethoxycarbonylacetylaminomethylthiazole (0.43 g) and 4N sodium hydroxide (3 ml), methanol (5 ml) and water (5 ml) was stirred at ambient temperature for 4.5 hours. After allowing to cool to room temperature, the mixture was poured to water, and the aqueous layer was adjusted to pH 1 with 10% hydrochloric acid, and extracted with diethyl ether. The organic layer was washed with water and brine, and dried over magnesium sulfate and treated with activated charcoal. After filtration, the filtrate was evaporated in vacuo. The resulting residue was triturated with isopropyl ether and diethyl ether, to give 4,5-bis(4-methoxyphenyl)-2-(carboxyacetylaminomethyl)thiazole (0.23 g).

mp: 126°–130° C.

IR (Nujol): 1735, 1670, 1610, 1570, 1510 cm$^{-1}$

NMR (DMSO-d$_6$, δ): 3.24 (2H, s), 3.74 (3H, s), 3.77 (3H, s), 4.57 (2H, d, J=5.9Hz), 6.87 (2H, d, J=8.8Hz), 6.94 (2H, d, J=8.8Hz), 7.23 (2H, d J=8.8Hz), 7.36 (2H, d, J=8.8Hz), 8.98 (1H, t, J=5.9Hz)

MASS (M/Z): 368 (M+-CO$_2$)

Example 29

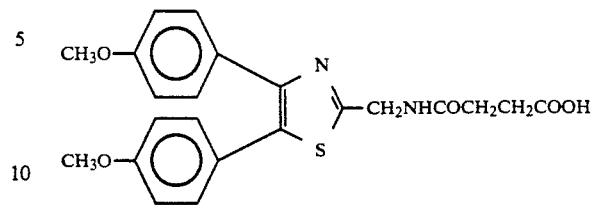

4,5-Bis(4-methoxyphenyl)-2-(3-carboxypropionylaminomethyl)thiazole was obtained according to a similar manner to that of Example 28.

mp: 110°–116° C.

IR (Nujol): 3310, 1710, 1650, 1615, 1540, 1520 cm$^{-1}$

NMR (DMSO-d$_6$, δ): 2.3–2.6 (4H, m), 3.74 (3H, s), 3.77 (3H, s), 4.53 (2H, d, J=5.9Hz), 6.88 (2H, d, J=8.8Hz), 6.95 (2H, d, J=8.8Hz), 7.23 (2H, d, J=8.8Hz), 7.36 (2H, d, J=8.8Hz), 8.82 (1H, t, J=5.9Hz)

MAS (M/Z): 426 (M+)

What we claim is:

1. A compound of the formula:

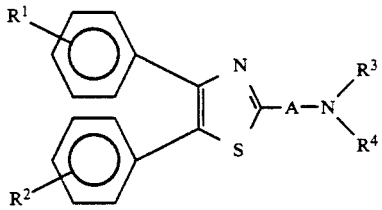

wherein A is lower alkylene or carbonyl,

R$^1$ and R$^2$ are each halogen, lower alkyloxy, lower alkylthio or lower alkylsulfinyl;

R$^3$ is an acyl moiety of an aliphatic carboxylic or carbamic acid; and

R$^4$ is hydrogen, lower alkyl, amidino or an acyl moiety of an aliphatic carboxylic or carbamic acid, or a pharmaceutically acceptable salt thereof.

2. The compound of claim 1, wherein

R$^3$ is lower alkanoyl, carboxyl(lower)alkanoyl, esterified carboxy(lower)alkanoyl, lower alkylthio(lower)alkanoyl, lower alkoxycarbonyl(lower)alkanoyl, carbamoyl or lower alkylcarbamoyl, and R$^4$ is hydrogen, lower alkyl, amidino, lower alkanoyl, carboxy(lower)alkanoyl, esterified carboxy(lower)alkanoyl, lower alkylthio(lower)alkanoyl, lower alkoxycarbonyl(lower)alkanoyl, carbamoyl or lower alkylcarbamoyl.

3. The compound of claim 2, wherein

R$^3$ is lower alkanoyl, carboxy(lower)alkanoyl, lower alkylthio(lower)alkanoyl, lower alkoxycarbonyl(lower)alkanoyl, carbamoyl or lower alkylcarbamoyl, and R$^4$ is hydrogen, lower alkyl, amidino, lower alkanoyl, carboxy(lower)alkanoyl, lower alkylthio(lower)alkanoyl, lower alkoxycarbonyl(lower) alkanoyl, carbamoyl or lower alkylcarbamoyl.

4. The compound of claim 3, wherein

A is lower alkylene,

R$^1$ and R$^2$ are each lower alkyloxy, and

R$^4$ is hydrogen.

5. The compound of claim 1 which is 4,5-bis(4-methoxyphenyl)-2-(3-isopropylureidomethyl)thiazole.

* * * * *